(12) United States Patent
Huang et al.

(10) Patent No.: US 8,836,940 B2
(45) Date of Patent: Sep. 16, 2014

(54) TEST APPARATUS FOR LIQUID CRYSTAL DISPLAY

(75) Inventors: Teng-Tsung Huang, New Taipei (TW); Guo-Jun Yu, Shenzhen (CN); Yong-Bing Hu, Shenzhen (CN); Yuan-Zhao Li, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 346 days.

(21) Appl. No.: 13/274,555

(22) Filed: Oct. 17, 2011

(65) Prior Publication Data

US 2012/0188537 A1 Jul. 26, 2012

(30) Foreign Application Priority Data

Jan. 25, 2011 (CN) .......................... 2011 1 0026870

(51) Int. Cl.
*G01N 21/01* (2006.01)
*G02F 1/13* (2006.01)
*G01N 21/95* (2006.01)

(52) U.S. Cl.
CPC ...... *G02F 1/1309* (2013.01); *G01N 2021/9513* (2013.01)
USPC ......................................... 356/244; 356/138

(58) Field of Classification Search
CPC ...................... G01N 2021/9513; G02F 1/1309
See application file for complete search history.

(56) References Cited

U.S. PATENT DOCUMENTS

| | | | | |
|---|---|---|---|---|
| 5,734,158 A * | 3/1998 | Nagashima et al. | ........... | 250/225 |
| 6,232,616 B1 * | 5/2001 | Chen et al. | ..................... | 356/244 |
| 7,426,022 B2 * | 9/2008 | Oka | ............................... | 356/218 |
| 7,889,311 B2 * | 2/2011 | Lee | .......................... | 324/760.01 |
| 2004/0065155 A1 * | 4/2004 | Liu et al. | ......................... | 73/798 |
| 2005/0018897 A1 * | 1/2005 | Choi et al. | ..................... | 382/141 |
| 2006/0215159 A1 * | 9/2006 | Smith | ............................ | 356/367 |
| 2006/0220670 A1 * | 10/2006 | Huang et al. | .................. | 356/632 |
| 2007/0001710 A1 * | 1/2007 | Park et al. | ..................... | 324/770 |
| 2007/0153226 A1 * | 7/2007 | Lee | ................................ | 349/192 |
| 2009/0278563 A1 * | 11/2009 | Kuo | ............................... | 324/770 |

FOREIGN PATENT DOCUMENTS

| | | |
|---|---|---|
| CN | 2643278 Y | 9/2004 |
| TW | 576537 U | 2/2004 |
| TW | M247818 | 10/2004 |

* cited by examiner

*Primary Examiner* — Kara E Geisel
*Assistant Examiner* — Juan D Valentin, II
(74) *Attorney, Agent, or Firm* — Novak Druce Connolly Bove + Quigg LLP

(57) ABSTRACT

A test apparatus is configured for testing a notebook including a liquid crystal display section and a body section. The positioning structure includes an optical testing module, an adjustable OTM mount, a fine-tuning module, a clamping module and a adjustable LCD mount. The optical testing module tests the liquid crystal display section, and is mounted to the adjustable OTM mount for moving the optical testing module. The optical testing module is attached to the fine-tuning module. The clamping module is for clamping the notebook. The adjustable LCD mount is mounted to the clamping module, and rotates the notebook relative to the optical testing module.

11 Claims, 5 Drawing Sheets

TEST APPARATUS FOR LIQUID CRYSTAL DISPLAY

BACKGROUND

1. Technical Field

The present disclosure generally relates to test apparatus, and particularly to a test apparatus for testing a liquid crystal display of a notebook computer.

2. Description of Related Art

The viewing cone is an important parameter of liquid crystal displays (LCDs), such as those used in notebook computer, and is usually measured to ensure performance In order to measure the viewing cone of notebook mounted LCDs, the notebook computer is mounted on a test apparatus and moved about to determine the scope or range of the viewing cone.

However, the known test apparatus is awkward to move, making testing slower and more susceptible to operator error.

Therefore, there is room for improvement within the art.

BRIEF DESCRIPTION OF THE DRAWINGS

Many aspects of the test apparatus can be better understood with reference to the following drawings. The components in the drawings are not necessarily to scale, the emphasis instead being placed upon clearly illustrating the test apparatus. Moreover, in the drawings, like reference numerals designate corresponding parts throughout the several views.

DETAILED DESCRIPTION

Figure 1:
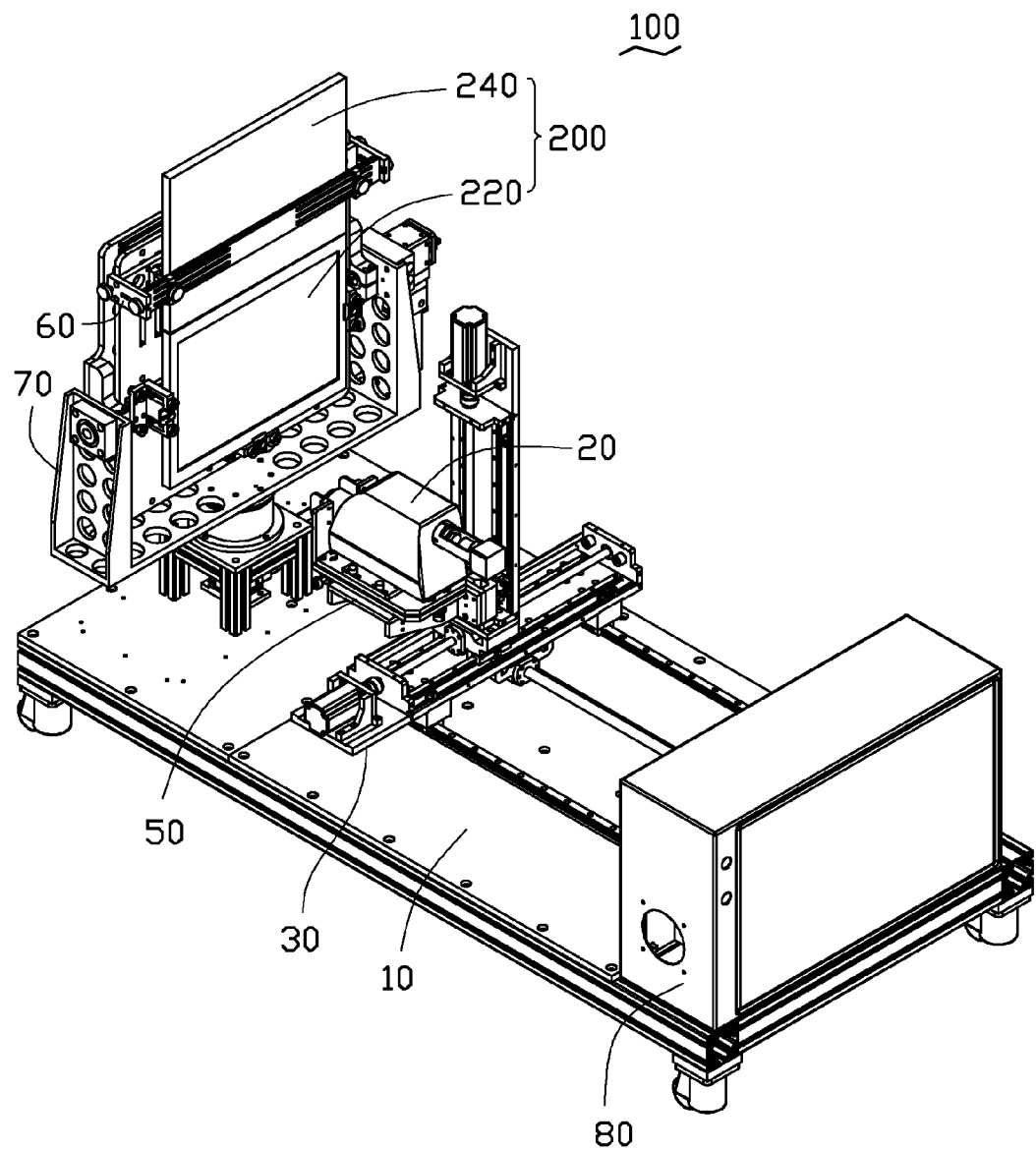
FIG. 1 is a schematic view of a test apparatus according to an exemplary embodiment.
Figure 2:
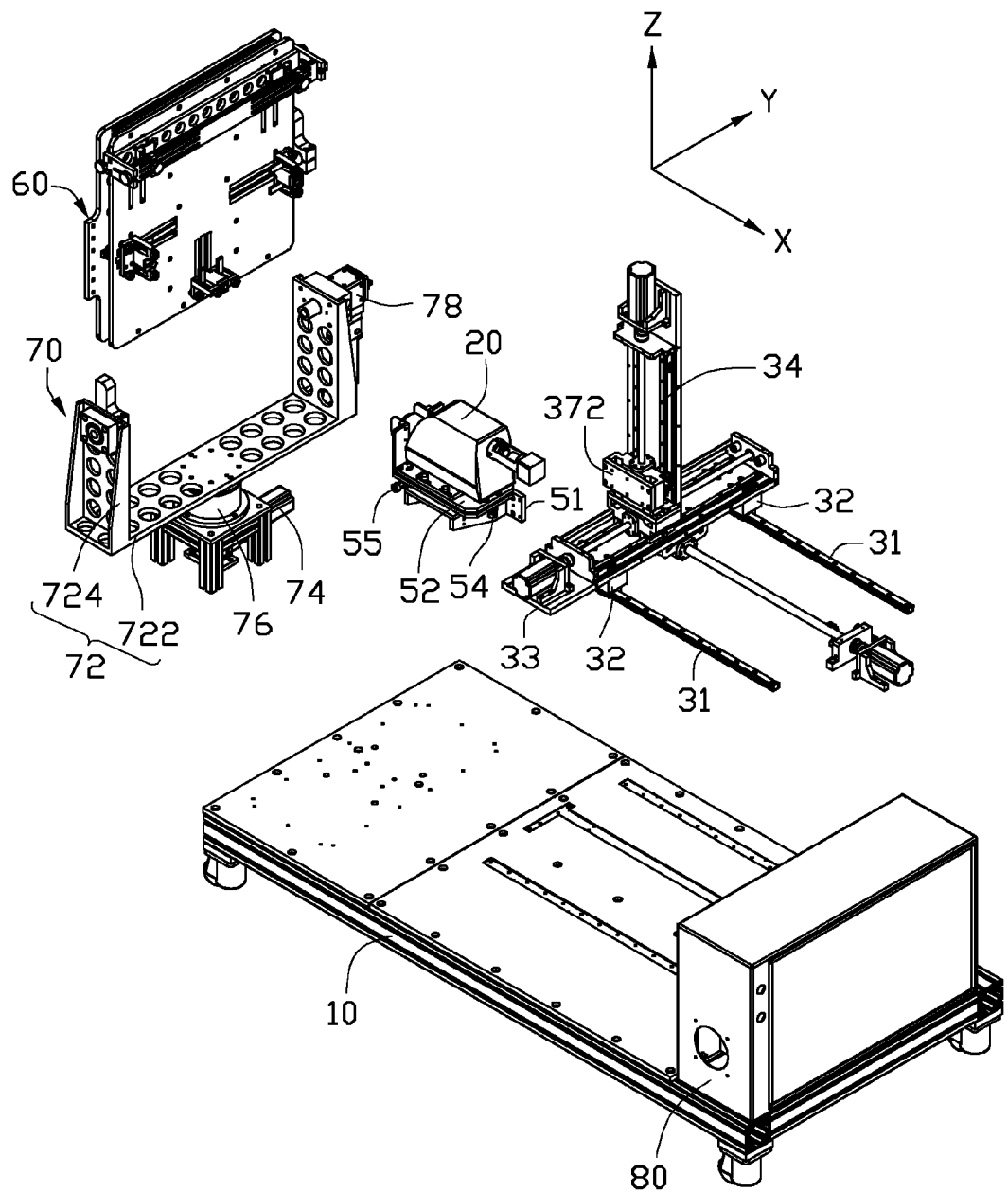
FIG. 2 is an exploded view of the test apparatus shown in FIG. 1.

FIGS. 1 to 2 show an exemplary embodiment of a test apparatus 100 for testing optical performances of a liquid crystal display of a notebook computer 200, such as visible angle. The notebook 200 is an exemplary application for the purposes of describing details of the test apparatus 100 of an exemplary embodiment. The notebook 200 includes a liquid crystal display (LCD) section 220 and a body section 240 hinged to the LCD section 220.

The test apparatus 100 includes an optical testing module (OTM) 20, an adjustable OTM mount 30, a fine-tuning module 50, a clamping module 60, an adjustable LCD mount 70, and a control box 80 all supported on a worktable 10. The adjustable OTM mount 30 and the fine-tuning module 50 are configured for positioning the optical testing module 20 relative to the LCD section 220. The clamping module 60 is configured for clamping the notebook 200, and the adjustable LCD mount 70 is configured for rotating the notebook 200 relative to the optical testing module 20.

The optical testing module 20 is for computing optical parameters of the LCD section 220. In this embodiment, the optical testing module 200 is positioned on the fine-tuning module 50, and is spaced from the notebook 200 about 500 millimeters.

Figure 3:
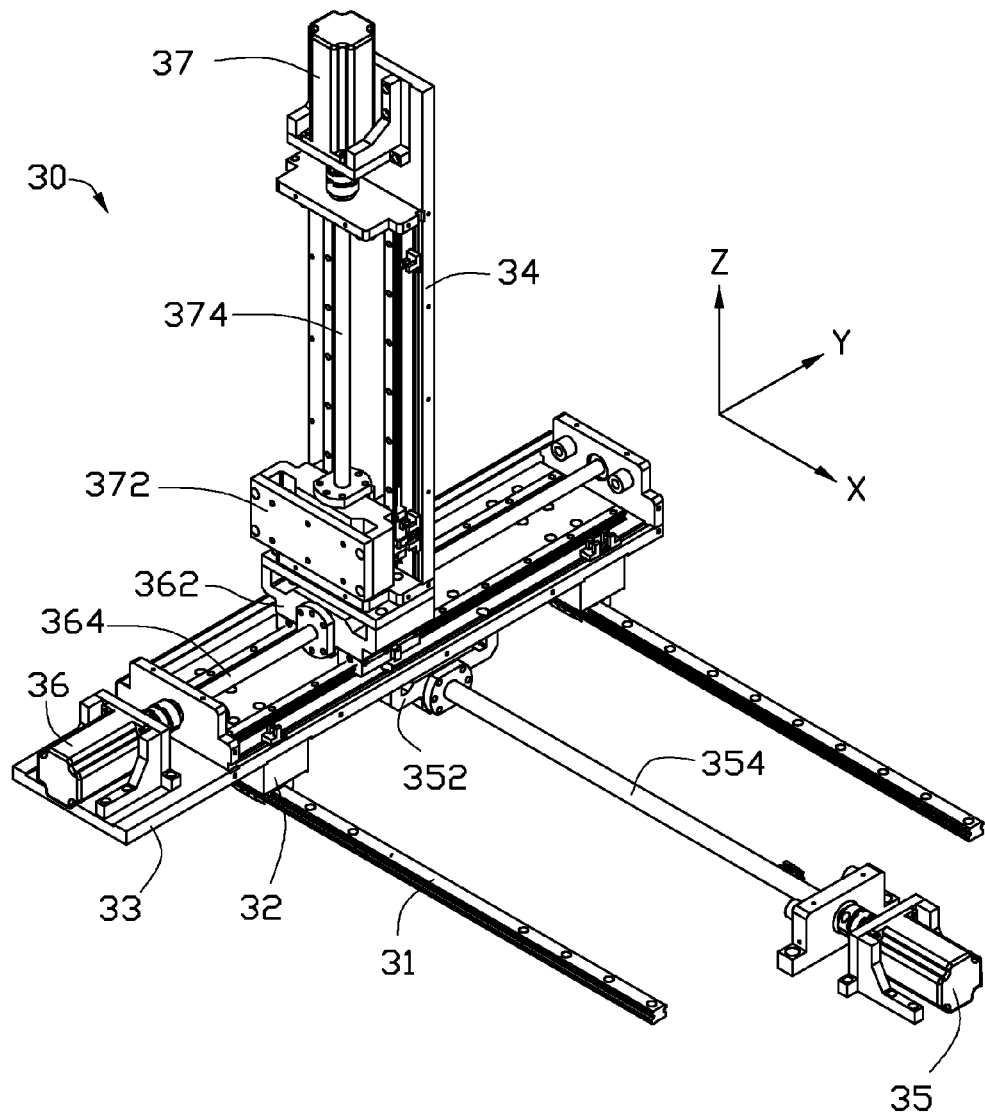
FIG. 3 is an assembled schematic view of the adjustable OTM mount shown in FIG. 2.

The adjustable OTM mount 30 is for positioning the fine-tuning module 50 and the optical testing module 20. Referring to FIG. 3, the adjustable OTM mount 30 includes two guide rails 31, two slide blocks 32, a support plate 33, a side plate 34, a first motor 35, a first connecting block 352, a first shaft 354, a second motor 36, a second connecting block 362, a second shaft 364, a third motor 37, a third connecting block 372, and a third shaft 374. An X-Y-Z coordinate system is shown in FIG. 3. The first motor 35 drives the support plate 36 to move along the X-axis. The second motor 36 drives the second, third connecting blocks 362, 372 to move along the Y-axis. The third motor 37 drives the third connecting blocks 372 to move along the Z-axis. The optical testing module 20 and the fine-tuning module 50 are mounted to the third connecting block 372. Thus, the first, second, third motors 35, 36, 37 can change the position of the optical testing module 20.

The two guide rails 31 are arranged in parallel to each other on the worktable 10. The slide blocks 32 are slidably engaged with the guide rails 31. The two slide blocks 32 are mounted on an underside of the support plate 33. The first connecting block 352 is formed under the support plate 33, and is positioned between the slide blocks 32. One end of the first shaft 354 is connected to the first motor 35, and the other end is connected to the first connecting block 352. When the first motor 35 drives the first shaft 354 to retract or advance along the X-axis, the first connecting block 352 drives the support plate 33 to move. The second motor 36 is mounted on the support plate 33. One end of the second shaft 364 is connected to the second motor 36, and the other end is connected to the second connecting block 362. The side plate 34 is vertically positioned on the second connecting block 362. The third motor 37 is mounted on the side plate 34. One end of the third shaft 374 is connected to the third motor 37, and the other end is connected to the third connecting block 372. When the second motor 36 drives the second shaft 364 to retract or advance along the Y-axis, the second connecting block 362 drives the side plate 34 to move. When the third motor 37 drives the third shaft 374 to retreat or advance along Z-axis, the third connecting block 372 moves the fine-tuning module 50 and the optical testing module 20.

Referring to FIG. 2, the fine-tuning module 50 is for finely adjusting the position of the optical testing module 20. The fine-tuning module 50 includes a seat 51, two adjusting plates 52, a first adjusting bolt 54, and a second adjusting bolt 55. The seat 51 is mounted to the third connecting block 372 for moving together with the fine-tuning module 50. The two adjusting plates 52 are positioned on the seat 51, and overlap each other. The optical test module 20 is secured on the adjusting plates 52. The first adjusting bolt 54 and the second adjusting bolt 55 are engaging with the adjusting plates 52. The Y-direction and Z-direction distances of the adjusting plates 52 can be changed by rotating the first, second adjusting bolts 54, 55 to adjust the position of the optical testing module 20.

Figure 4:
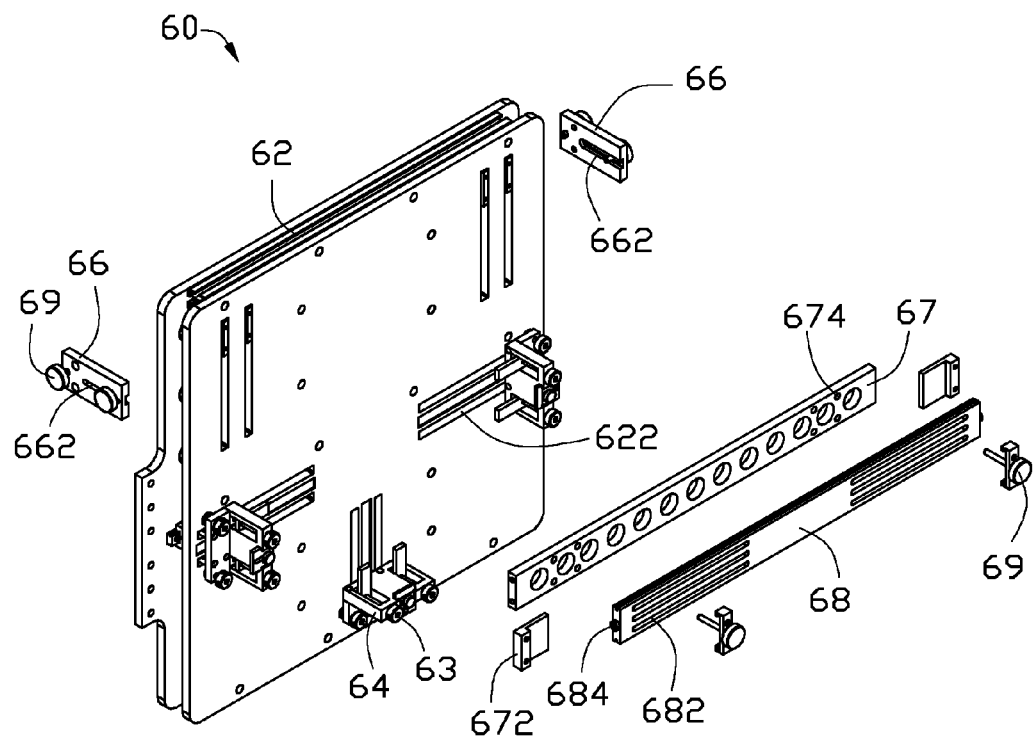
FIG. 4 is an exploded view of the clamping module shown in FIG. 2.
Figure 5:
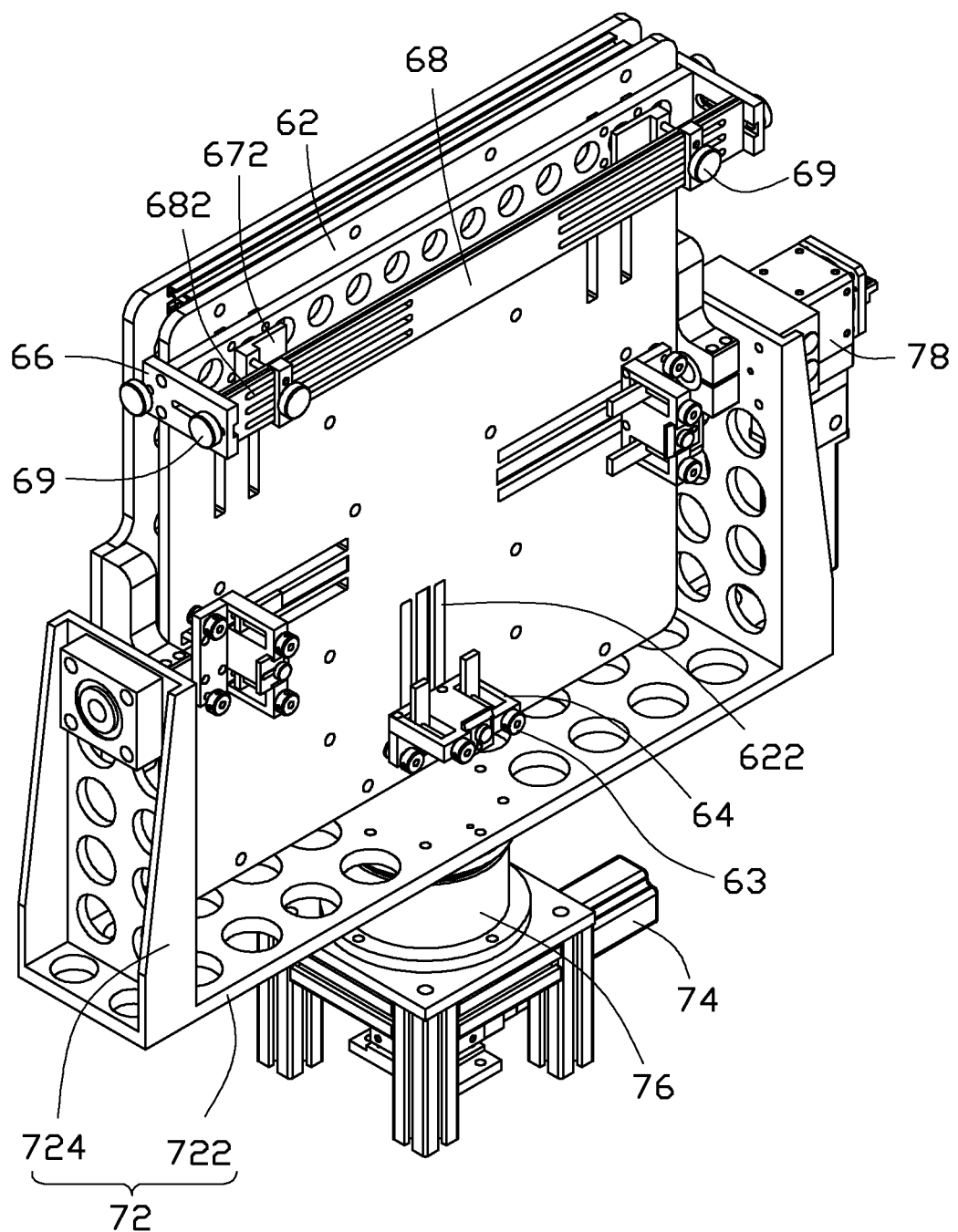
FIG. 5 is an assembled view of the clamping module attached to the adjustable LCD mount shown in FIG. 2.

Referring to FIGS. 4 and 5, the clamping module 60 includes a base 62, a number of first buttons 63, three limiting blocks 64, two stoppers 66, a beam 67, two resisting blocks 672, a clamping plate 68, and a number of second buttons 69. The base 62 defines three groups of first slots 622 at different directions. Each limiting block 64 is engaged in a corresponding group of first slots 622 by the first buttons 63 for slidably attaching the limiting blocks 64 to the base 61. The limiting blocks 64 may be adjusted for clamping different size LCD sections 220. Each stopper 66 is mounted at opposite sides of the base 62 by one second button 69. Each stopper 66 defines a second slot 662. Two posts 684 are formed at opposite ends of the clamping plate 68. One second button 69 extends through the second slot 662 of the stopper 66, and is mounted to a corresponding post 684 for rotatably attaching the clamping plates 68 to the stoppers 66. The beam 67 is mounted on the base 62, and defines two pairs of holes 674 at opposite sides. The clamping plate 68 defines a number of slits 682. The second buttons 69 extend through the slits 682, the resisting blocks 672 and the holes 674 for positioning the resisting blocks 672 between the beam 67 and the clamping plate 68. Since the clamping plate 68 can rotate relative to the stoppers 66, the angle of the clamping plate 68 relative to the base 62 is adjustable. Thus, the body section 240 of the notebook 200 does not need to be detached from the LCD section 220, and may directly be inserted between the beam 67 and the clamping plate 68. The resisting blocks 672 can be adjusted for clamping the body section 240.

The adjustable LCD mount 70 is for rotating the notebook 200 relative to the optical testing module 20. Referring to FIGS. 2 and 5, the adjustable LCD mount 70 includes a frame 72, a first drive member 74, a rotational member 76, and a second drive member 78. The frame 72 includes a connecting board 724 and two side boards 724 integrally formed together. The side boards 724 are respectively mounted to the base 62 of the clamping module 60. The first drive member 74 is mounted on the worktable 10. One end of the rotational member 76 is mounted to the connecting board 724, and the other end is connected to the first drive member 74. The first, second drive members 74, 78 are electrically connected to the control box 80. The first drive member 74 rotates the rotational member 76, and the frame 72 is driven to rotate around the Z-axis. The second drive member 78 is mounted to one of the side boards 724 for rotating the frame 72 along the Y-axis.

In testing, the LCD section 220 is latched to the clamping module 60 using the limiting blocks 64, and the body section 240 is latched between the beam 67 and the clamping plate 69. The limiting blocks 64 and the resisting blocks 672 may be adjusted according to the size of the notebook 200. After the notebook 200 is positioned on the test apparatus 100, the optical testing module 20 is positioned relative to the notebook 200. Rough positioning of the module 20 is achieved using the first, second, third motors 35, 36, 37. Then the position of the optical testing module 20 is fine-tuned by rotating the first, second adjusting bolts 54, 55.

The test apparatus 100 can replace manual positioning of the notebook 200 during known viewing cone test procedures. The notebook 200 can be rotated by the adjustable LCD mount 70 relative to the optical testing module 20 to required positions automatically. As the first drive member 74 rotates the notebook 200 around the Z-axis, and the second drive member 78 rotates the notebook 200 along the Y-axis, the OTM 20 processes light rays from the LCD 220 to compute the viewing cone of the LCD 220.

It is to be understood, however, that even through numerous characteristics and advantages of the present disclosure have been set forth in the foregoing description, together with details of the structure and function of the disclosure, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. A test apparatus configured for testing a notebook computer having a liquid crystal display section and a body section, comprising:
    an optical testing module processing light rays from the liquid crystal display section to compute a viewing cone of the liquid crystal display section for testing the liquid crystal display section;
    an adjustable optical testing module mount, the optical testing module configured to be mounted to the adjustable optical testing module mount so that the optical testing module can be moved;
    a fine-tuning module mounted to the adjustable optical testing module mount, the optical testing module being further attached to the fine-tuning module;
    a clamping module configured to clamp the liquid crystal display section of the notebook computer to allow the liquid crystal display section to be visible to the optical testing module; and
    an adjustable crystal display mount mounting the clamping module for rotating the liquid crystal display section of the notebook computer relative to the optical testing module so that the optical testing module processing the light rays from the liquid crystal display section;
    wherein the clamping module includes a base and three limiting blocks, the limiting blocks are slidably attached to the base and configured to latch onto the liquid crystal display section, wherein the clamping module includes two stoppers and a clamping plate, each stopper is mounted at opposite sides of the base, and the clamping plate is rotatably attached to the stoppers.

2. The test apparatus as claimed in claim 1, wherein the adjustable optical testing module mount includes a first motor, a second motor, and a third motor, the first motor, the second motor and the third motors drive the optical testing module to move along a first direction, a second direction and a third direction.

3. The test apparatus as claimed in claim 2, wherein the adjustable optical testing module mount includes a support plate, a side plate, a first connecting block, a second connecting block, a third connecting block, the first connecting block is formed under the support plate, and is driven by the first motor, the second motor is mounted on the support plate, and drives the second connecting block, the side plate is positioned on the second connecting block, the third connecting block is mounted with the fine-tuning module, and the third motor is mounted on the side plate for driving the third connecting block.

4. The test apparatus as claimed in claim 3, wherein the fine-tuning module includes a seat, the seat is mounted to the third connecting block for moving together with the fine-tuning module.

5. The test apparatus as claimed in claim 4, wherein the fine-tuning module includes two adjusting plates, a first adjusting bolt and a second adjusting bolt, the two adjusting plates are positioned on the seat, and are overlapping each other, the optical test module is secured on the adjusting plates, and a Y-direction and Z-direction distances of the two adjusting plates are changed by rotating the first adjusting bolt and the second adjusting bolt.

6. The test apparatus as claimed in claim 1, wherein the clamping module includes a beam and two resisting blocks, the beam is mounted on the base, and the resisting blocks are positioned between the beam and the clamping plate.

7. The test apparatus as claimed in claim 6, wherein the adjustable crystal display mount includes a first drive member and a second drive member mounted to the base, and the first drive member and the second drive member rotate the base and the notebook.

8. The test apparatus as claimed in claim 7, wherein the adjustable crystal display mount includes a frame, the frame includes a connecting board and two side boards integrally formed together, the side boards are respectively mounted to the base of the clamping module.

9. A test apparatus comprising:
    an optical testing module processing light rays from a liquid crystal display section to compute a viewing cone of the liquid crystal display section for testing the liquid crystal display section of a notebook computer;
an adjustable optical testing module mount moving the optical testing module;
a fine-tuning module mounted to the adjustable optical testing module mount, the optical testing module being further attached to the fine-tuning module;
a clamping module configured to clamp the liquid crystal display section of the notebook computer to allow the liquid crystal display section to be visible to the optical testing module; and
an adjustable crystal display mount mounting the clamping module, for rotating the liquid crystal display section of the notebook computer relative to the optical testing module so that the optical testing module processing the light rays from the liquid crystal display section;
wherein the clamping module includes a base and three limiting blocks, the limiting blocks are slidably attached to the base and configured to latch onto the liquid crystal display section; wherein the clamping module includes two stoppers and a clamping plate, each stopper is mounted at opposite sides of the base, and the clamping plate is rotatably attached to the stoppers.

10. The test apparatus as claimed in claim 9, wherein the clamping module includes a beam and two resisting blocks, the beam is mounted on the base, and the resisting blocks are positioned between the beam and the clamping plate.

11. The test apparatus as claimed in claim 10, wherein the adjustable crystal display mount includes a first drive member and a second drive member mounted to the base, and the first drive member and the second drive member rotate the base and the notebook.

\* \* \* \* \*